(12) United States Patent
Swartling et al.

(10) Patent No.: US 8,582,841 B2
(45) Date of Patent: Nov. 12, 2013

(54) SYSTEM AND METHOD FOR PRE-TREATMENT PLANNING OF PHOTODYNAMIC LIGHT THERAPY

(75) Inventors: Johannes Swartling, Lund (SE); Sune Svanberg, Lund (SE); Johan Axelsson, Lund (SE); Stefan Andersson-Engels, Lund (SE); Ann Johansson, Lund (SE); Jarl Ebbe Johansson, legal representative, Lund (SE)

(73) Assignee: SpectraCure AB, Lund (SE)

( * ) Notice: Subject to any disclaimer, the term of this patent is extended or adjusted under 35 U.S.C. 154(b) by 384 days.

(21) Appl. No.: 12/836,497

(22) Filed: Jul. 14, 2010

(65) Prior Publication Data
US 2010/0329524 A1 Dec. 30, 2010

Related U.S. Application Data

(63) Continuation-in-part of application No. 12/377,595, filed as application No. PCT/EP2007/058477 on Aug. 15, 2007, which is a continuation of application No. PCT/EP2010/051605, filed on Feb. 9, 2010.

(60) Provisional application No. 60/837,751, filed on Aug. 15, 2006, provisional application No. 60/883,738, filed on Jan. 5, 2007, provisional application No. 60/942,630, filed on Jun. 7, 2007, provisional application No. 61/151,129, filed on Feb. 9, 2009.

(51) Int. Cl.
*G06K 9/00* (2006.01)

(52) U.S. Cl.
USPC .......................................................... 382/128

(58) Field of Classification Search
USPC .................................................. 382/128, 154
See application file for complete search history.

(56) References Cited

U.S. PATENT DOCUMENTS

| 5,292,320 | A | 3/1994 | Brown et al. |
| 5,318,024 | A | 6/1994 | Kittrell et al. |

(Continued)

FOREIGN PATENT DOCUMENTS

| EP | 1 334 748 A | 8/2003 |
| EP | 1 470 837 A2 | 10/2004 |

(Continued)

OTHER PUBLICATIONS

Weersink, et al., "Techniques for Delivery and Monitoring of TOOKAD (WST09)—Mediated Photodynamic Therapy of the Prostate: Clinical Experience and Practicalities", Proceedings of the SPIE, The International Society for Optical Engineering, vol. 5689, No. 1, (2005), pp. 112-122.

(Continued)

*Primary Examiner* — Tom Y Lu
(74) *Attorney, Agent, or Firm* — Knobbe Martens Olson & Bear LLP (57) ABSTRACT

A system for providing interstitial photodynamic and/or photothermal therapy on a region of tissue in a body, comprising at least one light source adapted to deliver a therapeutic light to the region of tissue, such that the light source is interstitially inserted into the tissue for interaction with a photosensitizer agent and/or for providing a controlled thermal environment of the tissue; and a unit for determining an optimized number of the light sources and individual position of each of the light sources in the region of tissue as well as individual control parameters for each of the light sources.

20 Claims, 3 Drawing Sheets

(56) References Cited

U.S. PATENT DOCUMENTS

| | | | |
|---|---|---|---|
| 5,527,349 | A | 6/1996 | Landry et al. |
| 6,138,046 | A * | 10/2000 | Dalton .................... 600/476 |
| 6,366,719 | B1 * | 4/2002 | Heath et al. .............. 385/31 |
| 7,037,325 | B2 * | 5/2006 | Svanberg et al. ........... 607/89 |
| 7,988,715 | B2 * | 8/2011 | Johansson et al. .......... 607/88 |
| 2004/0267335 | A1 * | 12/2004 | Tulip et al. .............. 607/89 |
| 2006/0282136 | A1 | 12/2006 | Tulip et al. |
| 2007/0282404 | A1 * | 12/2007 | Cottrell et al. ........... 607/89 |
| 2008/0033339 | A1 | 2/2008 | Tulip et al. |
| 2008/0221647 | A1 | 9/2008 | Chamberland et al. |

FOREIGN PATENT DOCUMENTS

| | | |
|---|---|---|
| EP | 1 637 182 A | 3/2006 |
| WO | WO 99/06113 A | 2/1999 |
| WO | WO 01/97902 A2 | 12/2001 |
| WO | WO 03/041575 A1 | 5/2003 |
| WO | WO 2004/030761 A1 | 4/2004 |
| WO | WO 2004-112902 | 12/2004 |
| WO | WO 2008/020050 A1 | 2/2008 |
| WO | WO 2008/062000 | 5/2008 |
| WO | WO 2008/103982 A2 | 8/2008 |
| WO | WO 2008/152076 A2 | 12/2008 |

OTHER PUBLICATIONS

Johansson et al., "System for Integrated Interstitial Photodynamic Therapy and Dosimetric Monitoring", Proceedings of the SPIE—The International Society for Optical Engineering, vol. 5689, No. 1, (2005), pp. 130-140.

Johnansson et al., "In vivo Measurement of Parameters of Dosimetric Importance during Interstitial Photodynamic Therapy of Thick Skin Tumors", Journal of Biomedical Optics SPIE USA, vol. 11, No. 3, (May 2005), pp. 34029-1.

Andersson-Engels et al., "Integrated System for Interstitial Photodynamic Therapy", Proceedings of SPIE—The International Society for Optical Engineering SPIE—Int. Soc Opt Eng USA, vol. 5123, (2003), pp. 293-302.

Svensson et al., "In vivo Optical Characterization of Human Prostate Tissue Using Near-Infrared Time-Resolved Spectroscopy", Journal of Biomedical Optics SPIE USA, vol. 12, No. 1, (Jan. 2007) pp. 14022-1.

Dougherty et al., "Photodynamic Therapy", Journal of the National Cancer Institute, vol. 90, No. 12, (Jun. 17, 1998), pp. 889-905.

Johansson et al., "Realtime Light Dosimetry Software Tools for Interstitial Photodynamic Therapy of the human Prostrate", Medical Physics, AIP, Melville, NY, US, vol. 34, No. 11, (Oct. 19, 2007), pp. 4309-4321.

Altschuler Martin et al., Optimized interstitial PDT prostate treatment planning with the Cimmino feasibility algorithm. Medical Physics, AIP, vol. 32, No. 12, Nov. 9, 2005.

International Search Report and Written Opinion issued in PCT Application No. PCT/EP2010/051605, mailed May 7, 2010.

Johansson, et al. (2002) Feasibility study of a system for combined light dosimetry and interstitial photodynamic treatment of massive tumors. Applied Optics; 41:7; 462-1468.

EPO Extended Search Report, Application No. EP 10162517.6 dated Dec. 3, 2010, 9 pages.

* cited by examiner

SYSTEM AND METHOD FOR PRE-TREATMENT PLANNING OF PHOTODYNAMIC LIGHT THERAPY

CROSS REFERENCE TO RELATED APPLICATIONS

This application is a continuation-in-part of U.S. application Ser. No. 12/377,595, filed Feb. 13, 2009, which is the US National Phase filing of PCT/EP2007/058477, filed Aug. 15, 2007, which claims priority to U.S. Provisional Application No. 60/837,751, filed Aug. 15, 2006, 60/883,738, filed Jan. 5, 2007, and to U.S. Provisional Application No. 60/942,630, filed Jun. 7, 2007. This application is also a continuation of PCT/EP2010/051605, filed Feb. 9, 2010, which claims priority to U.S. Provisional Patent Application No. 61/151,129, filed Feb. 9, 2009. The contents of all of these applications are incorporated herein by reference in their entireties.

FIELD OF THE INVENTION

This invention pertains in general to the field of photodynamic light therapy (PDT) and related systems, devices, computer program products and methods. More particularly the invention relates to planning, controlling and adjusting parameters in such a PDT system. Even more particularly, the invention refers to a system and method for pre-treatment and planning process parameters prior to therapy in an interstitial tumor PDT system.

BACKGROUND OF THE INVENTION

Photodynamic therapy (PDT) is a cancer treatment modality that has shown promising results in terms of selectivity and efficacy, see e.g. Dougherty T J, et. al.: Photodynamic therapy, Journal of the National Cancer Institute 1998; 90: 889-905.

PDT relies on the use of a photosensitizer agent being activated by light in the presence of oxygen, leading to the production of toxic singlet oxygen radicals. Tissue destruction results from apoptosis, necrosis and vascular damage caused by these toxic singlet oxygen radicals.

In order to achieve an efficient treatment, several fibers have been used to ascertain that all tumor cells are subjected to a sufficient dose of radiation so that the toxic singlet state is obtained.

A limited penetration in the tissue of the activating light is a general issue of PDT. Only tumors less than about 5 mm in thickness may be treated by surface irradiation. In order to treat thicker and/or deeper lying tumors, interstitial PDT (IPDT) may be utilized. In interstitial PDT, light-conducting optical fibers are brought into the tumor using, e.g., a syringe needle, in the lumen of which a fiber has been placed, which is for instance described in PCT/SE2006/050120 of the same applicant as the present application, which hereby is incorporated by reference in its entirety for all purposes. However, PCT/SE2006/050120 does not provide a guidance concerning an effective positioning of a plurality of such optical fibers in a region of tumor tissue.

To optimize the biological effect in interstitial PDT, an accurate dosimetry method is needed and further a specifically devised planning prior the actual treatment of subjects is needed.

A pre-treatment planning of PDT is disclosed in PCT/EP2007/058477 of the same applicant as the present application, which hereby is incorporated by reference in its entirety for all purposes. A Method is disclosed that constitutes pre-treatment modules for IPDT on a whole prostate glandular tissue. The method includes reconstruction of the target geometry and optimization of source fiber positions within this geometry prior to beginning IPDT. However, the method of PCT/EP2007/058477 may further be improved, in particular with regard to information or guidance concerning determination of parameters of importance for pre-treatment or planning of the PDT, as well as adjustment thereof to particular patient situations.

Hence, there is a need for an alternative, or improved advantageous method and/or system for initially presetting, controlling and adjusting light therapy and/or related parameters before and during PDT in vivo or in vitro. In particular, the pre-treatment positioning of light sources in relation to a region of treatment may be improved.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing systems, methods, and a computer program, according to the appended patent claims.

Even more particularly, the invention comprises a system, method, a computer program, and a medical workstation, incorporating a calculation method for determination of initial status, i.e. pre-treatment status, of tissue before the PDT treatment. The calculation method is based on an evaluation of at least one image data set related to the tumor or to a sensitizer, wherein said image data set is a combined or superimposed image data set from at least two different image modalities, such as MR and ultrasound.

A system is disclosed for providing interstitial photodynamic therapy on tissue in a body is provided. The system comprises functionality to superimpose 3D images of a region of treatment acquired from different modalities. An aggregated 3D image related to the region of treatment, e.g. a tumor site of the subject. The superimposed multi-dimensional image form basis for the pre-treatment procedure and planning process. A 4D image may be taken into consideration, wherein the fourth dimension is time, e.g. in order to take a spatial blood flow distribution into consideration. This may be used for calculating various 3D parameters over time. For instance, the calculation may be a 3D temperature discharge function, or a 3D washout factor of sensitizer or oxygen, or a 3D oxygen renewal parameter. Based on these calculations, positioning of at least one light source in the region of interest is optimized. According to an aspect of the invention, a system for providing interstitial photodynamic and/or photothermal therapy on a region of tissue in a body is disclosed. The system has at least one light source adapted to deliver a therapeutic light to said region of tissue in said tissue, wherein said light source is devised to be interstitially inserted into said tissue for interaction with a photosensitizer agent and/or for providing a controlled thermal environment of said tissue. Furthermore the system has a unit for determining an optimized number of said light sources and individual position of each of said light sources in said region of tissue as well as individual control parameters for each of said light sources based on 3D or 4D image data of said region of tissue acquired by at least one image modality.

In embodiments the 3D or 4D image data comprises said region of tissue is combined image data from at least two different image modalities. In embodiments the system is adapted to superimpose said 3D or 4D image data for obtaining said combined image data from at least two different image modalities. The determination may be made in a computer based virtual environment which allows for a user friendly planning and a reliable and improved medical procedure.

In embodiments the system has a unit for evaluating at least one photodynamic treatment parameter of said interstitial photodynamic therapy at said light source; a unit for modifying characteristics of said therapeutic light of said interstitial photodynamic therapy in response to the evaluation of said photodynamic treatment parameter; and a control unit that is arranged to restrict said delivery of therapeutic light treatment at least temporary in dependence of at least one attribute of one of said photodynamic treatment parameters.

The photodynamic treatment parameter may be a parameter related to a status of said tissue or of a photosensitizer agent in said tissue. The photodynamic treatment parameter may be an effective attenuation coefficient of said tissue.

The light source may be a distal end region of an optical fiber adapted to be inserted interstitially into said region of tissue. The distal end region may has a light diffuser such that said optical fiber is configured at the distal end to emit diffused light. Alternatively, the light source is an implantable light source.

In another aspect, a computer readable storage medium is provided having stored thereon a computer program comprising a plurality of code segments for planning interstitial photodynamic and/or photothermal therapy session on a region of tissue in a body. The computer program comprises a first code segment for evaluating at least two sets of 3D or 4D images of two different image modalities of the tumor site of a subject; a second code segment for aggregating said 3D or 4D images rendering a superimposed multi-dimensional image data set; and a third code segment for determining an optimized number of said light sources and individual position of each of said light sources in said region of tissue as well as individual control parameters for each of said light sources based on said superimposed image data set.

The system, method, and computer program may be applied in a computer based virtual planning environment. In the virtual planning environment, the positioning of light sources, such as optical fiber ends may be made. An optimized position and number of light sources may be determined automatically. Alternatively, or in addition, the position and number of light sources may be adjusted manually in the virtual planning environment.

In an aspect, a computer based method of virtually planning a interstitial photodynamic and/or photothermal therapy session on a region of tissue in a body in a virtual environment is provided. The method comprises the steps of providing 3D or 4D data of a region of interest from at least one imaging modality, such as two different image modalities; and determining a number and spatial distribution, position and spatial orientation of interstitial light sources in relation to said region of tissue for optimized treatment based on an optimized number of said light sources and individual position of each of said light sources in said region of tissue as well as individual control parameters for each of said light sources based on said superimposed image data set; and virtually planning said session on said determined number and spatial distribution, position and spatial orientation of said interstitial light sources.

The 3D or 4D data may comprise data for a region larger or substantially larger than the region of treatment, e.g. comprising a tumor. In this case, virtual planning may comprise virtual planning of affixing a surgical template on anatomically fixed positions, e.g. onto bone tissue. The surgical template comprises at least one guide unit, such as a guide cylinder, having a defined stop unit. For instance a guide cylinder may comprise a stop collar that is provided in relation to a corresponding mating collar of a syringe type optical fiber introducer, such that a defined direction and depth is given from the surgical template to the region of treatment.

Alternatively, or in addition, data for positioning the light sources may be provided for a robotic system automatically or semi-automatically positioning the light sources in the region of treatment tissue.

Alternatively, or in addition, data for positioning the light sources may be used for a realtime feedback during positioning, e.g. based on a image acquired during positioning, such as ultrasound based. Thus, an adaptation may be performed to the current patient situation when positioning the light sources. This is advantageous, for instance when the anatomical position should be changed since the initial acquisition of 3D data prior to the virtual planning of the number of light sources and position thereof.

The system may thus in another aspect be a system for providing interstitial photodynamic and/or photothermal therapy on a region of tissue in a body. The system has least one light source adapted to deliver a therapeutic light to said region of tissue in said tissue, wherein said light source is devised to be interstitially inserted into said tissue for interaction with a photosensitizer agent and/or for providing a controlled thermal environment of said tissue; and a unit for determining an optimized number of said light sources and individual position of each of said light sources in said region of tissue as well as individual control parameters for each of said light sources based on 3D or 4D image data of said region of tissue acquired by at least one image modality.

The 3D or 4D image data comprises said region of tissue and may be combined image data from at least two different image modalities.

As mentioned, the system may be adapted to provide said determination in a computer based virtual environment.

The system may comprise a unit for evaluating at least one photodynamic treatment parameter of said interstitial photodynamic therapy at said light source; a unit for modifying characteristics of said therapeutic light of said interstitial photodynamic therapy in response to the evaluation of said photodynamic treatment parameter; and a control unit that is arranged to restrict said delivery of therapeutic light treatment at least temporary in dependence of at least one attribute of one of said photodynamic treatment parameters.

The light source may be a distal end region of an optical fiber. The distal end region may comprise a light diffuser.

The light source may also be an implantable light source, such as a light diode, laser diode.

In an aspect, a computer based method of virtually planning a PDT session, comprises providing 3D or 4D data of a region of interest from at least one imaging modality, and determining a number and distribution of interstitial light sources for optimized treatment.

The method may comprise providing a template for position of the light sources in said region of interest.

The providing of a template may comprises producing said template based on production data that is output from said virtual planning.

Based on the virtual planning, the light sources are accordingly positioned in the region of treatment tissue.

This positioning may be provided by using a surgical template produced from production data that is output from said virtual planning. The production data may e.g. be provided in STL format. Production may be accomplished by free form methods, including rapid prototyping methods.

According to another aspect a computer program for processing by a computer is provided. The computer program comprises code segments for aggregating and accurately superimposing multidimensional images from different images modalities in a photodynamic pre-treatment of a subject, in a system for providing interstitial photodynamic therapy on tissue in a body. The computer program comprises a first code segment for evaluating at least two sets of multi-dimensional images of arbitrary image modality of the tumor site of a subject; a second code segment for aggregating said multi-dimensional images rendering a superimposed multi-dimensional; and a third code segment for determine positions of interstitial distal end of the optical fibers in said tumor of the subject.

Further embodiments of the invention are defined in the dependent claims, wherein features for the second and subsequent aspects of the invention are as for the first aspect mutatis mutandis.

Some embodiments provide for advantageous pre-treatment positioning of light sources in relation to a region of treatment may be improved.

Some embodiments of the invention provide for an improved accuracy of treatment, leading e.g. to avoidance of an undertreatment of a patient. Some embodiments of the invention also provide for increased patient safety by avoiding damage to healthy organs at risk.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE PREFERRED EMBODIMENT

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a PDT system and method, and in particular to an interstitial PDT system and method with reference to an embodiment of treatment of prostate cancer. However, it will be appreciated that the invention is not limited to this application but may be applied to many other organs, including for example liver, esophagus, pancreas, breast, brain, lung, trachea, eye, urinary tract, brain stem, spinal marrow, bone marrow, kidneys, stomach, intestines, pancreas, gall bladder, etc.

The treatment may also in addition or alternatively comprise photothermal treatment.

Photodynamic therapy (PDT) has become a clinically more accepted method for treating certain types of malignancies in various organs, partly due to advantages, such as the possibility of repeated treatment and restriction of the treatment-induced tissue damage to irradiated sites. The PDT effect is caused by a combination of treatment induced apoptosis and direct necrosis, vascular damage and possibly an elicited immune response, where the extent of tissue damage depends on the light dose, the tissue oxygenation and the sensitizer concentration. For PDT, clinical treatment protocols often rely on a light threshold model. This simplified model is based on the assumption that only tissue regions exposed to a light dose exceeding a pre-defined threshold are damaged. The threshold light dose is likely to depend on tissue type and photosensitizer used. From the point of view of the deposited light dose, it is essential to monitor the tissue optical properties before and during the PDT treatment. significant inter- and intra-patient variations of the absorption and scattering coefficients of prostate tissue have been measured by many groups. In addition, any treatment-induced variations in absorption and scattering, possibly due to changes in blood content and tissue oxygenation status, directly influence the light distribution during the course of the treatment Applying IPDT a range of changing conditions may occur. These may be time dependent and/or vary within a tissue as to natural variations of for example blood vessel and/or nerve path positions, which could render either an overtreatment with possible severe undesired effects, or an undertreatment implying a non sufficient effect of the treatment. By adapting initial characteristics of the anatomy of the prostatic gland more accurately, such patient variabilities are overcome and an adequate desired outcome of the therapy is provided. Furthermore, by configuring and using optical fibers which have a distal tip configured for emitting diffused light vs. the common point light source configuration. The distal ends of the optical fibre may be provided with a spreading device, such as a lens or a cone at the end of the optical fibre. Alternatively, the surface of the outer sector of the fibre may be ground to diffuse the light. This is referred to as a diffuser. Either a distal end of an optical fibre may comprises a diffuser, or an implanted light source may comprise a diffuser.

Figure 1:
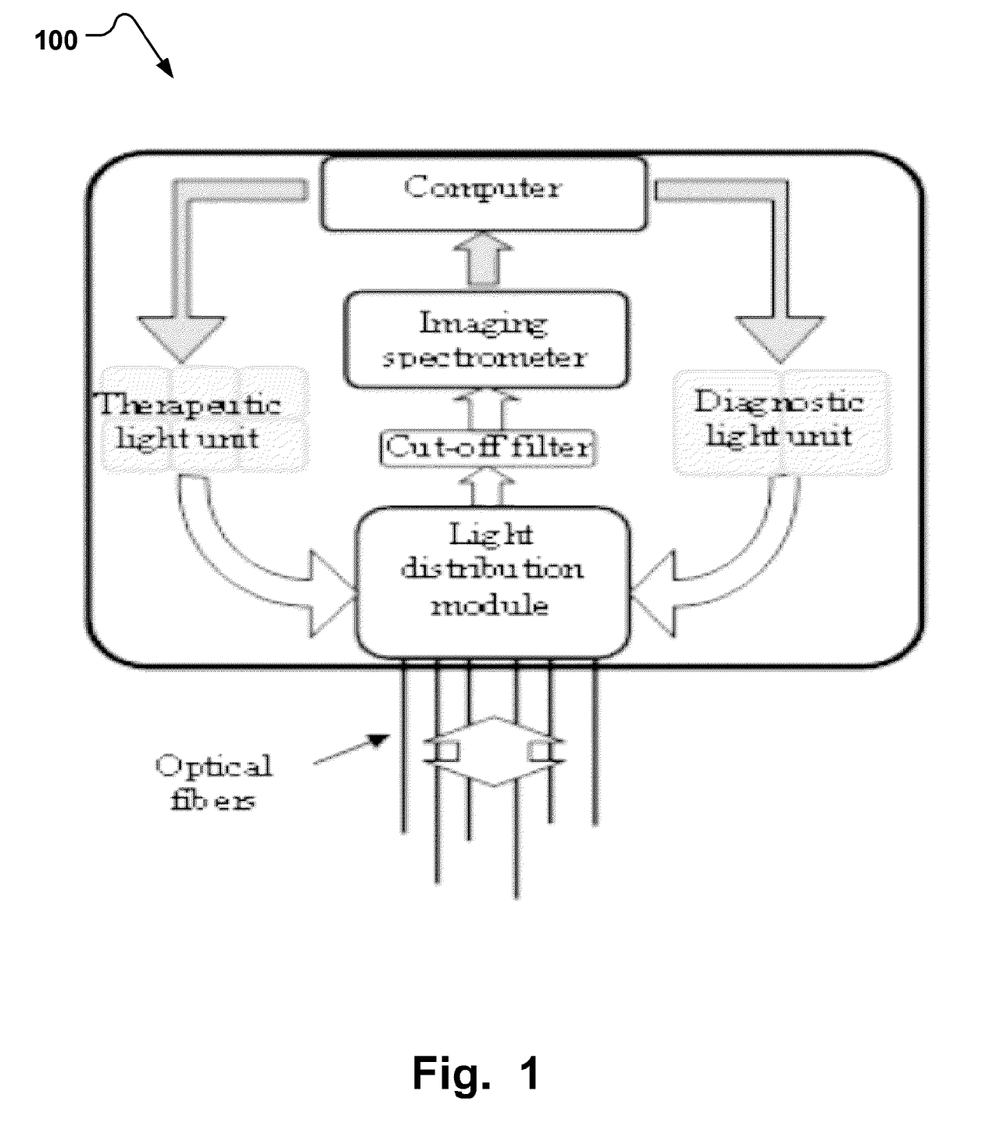
FIG. 1 is a schematic drawing of an interstitial PDT apparatus.

By using a diffuser, the light is disbursed more evenly in the treatment geometry, compared to a point source configured tip or light source. Consequently a more time efficient IPDT treatment will be the result as the light dose is more disbursed around the distal tip of the optical fiber causing less undesired tissue necrosis, adjacent the tip, for the same amount of energy, thus the light dose may the set to a higher level with a lesser treatment time as result. And by positioning the distal tips of the optical fibers in the region of treatment tissue, such as the prostate gland taken account of the different light distribution properties compared to point source a smaller number of optical fibers can be used to cover the same anatomical geometry to yield same treatment efficiency. Hence, less transcutaneous incisions have to be made, using optical fibers configured to emit diffused light. In this manner a surgical template, as described herein may be provided with less components, whereby manufacturing costs are reduced. FIG. 1 shows a general IPDT treatment scheme in which the invention is incorporated. Prior to the prostate IPDT treatment a transrectal ultra-sound investigation is performed to assess the geometry of the target tissue as well as nearby organs at risk (OAR). Cross-sectional slices are retrieved of the prostate geometry and adjacent tissue types. The slices form the basis for a three dimensional rendering of the tissue volume where the extent of the prostatic gland, urethra, rectum, upper and lower sphincters and the cavernous nerve bundles are delineated by the urologist. To further define the tissue, in and around the prostatic gland, additional image modalities may be used, e.g. MR, CT, SPECT, PET. The retrieved images from the different image modalities are superimposed to an aggregated 3D model of the geometry to be treated. Based on the 3D model of the geometry a random-search algorithm provides positions for the optical fibers. The optical fibers are then positioned at these positions, based on that virtual planning.

In a system for providing interstitial photodynamic therapy on tissue in a body is provided, the system comprises functionality to superimpose 3D images of a region of treatment acquired from different modalities. An aggregated 3D image related to the region of treatment, e.g. a tumor site of the subject. The superimposed multi-dimensional image form basis for the pre-treatment procedure and planning process. A 4D image may be taken into consideration, wherein the fourth dimension is time, e.g. in order to take a spatial blood flow distribution into consideration. This may be used for calculating various 3D parameters over time. For instance, the calculation may be a 3D temperature discharge function, or a 3D washout factor of sensitizer or oxygen, or a 3D oxygen renewal parameter. Based on these calculations, positioning of at least one light source in the region of interest is optimized.

The system, method, a computer program, and a medical workstation, may be applied in a computer based virtual planning environment. In the virtual planning environment, the positioning of light sources, such as optical fiber ends may be made. An optimized position and number of light sources may be determined automatically. Alternatively, or in addition, the position and number of light sources may be adjusted manually in the virtual planning environment.

The 3D or 4D data may comprise data for a region larger or substantially larger than the region of treatment, e.g. comprising a tumor. In this case, virtual planning may comprise virtual planning of affixing a surgical template on anatomically fixed positions, e.g. onto bone tissue. The surgical template comprises at least one guide unit, such as a guide cylinder, having a defined stop unit. For instance a guide cylinder may comprise a stop collar that is provided in relation to a corresponding mating collar of a syringe type optical fiber introducer, such that a defined direction and depth is given from the surgical template to the region of treatment.

The surgical template may be provided as a 3D structure adapted to that of an organ. The organ may be the organ to be treated. The surgical template is thus positionable in relation to the tissue to be treated.

The surgical template is based on the specific patient and the determined number of light sources/fibers. Treatment becomes thus advantageously efficient, user friendly to implement and reliable.

Alternatively, or in addition, data for positioning the light sources may be provided for a robotic system automatically or semi-automatically positioning the light sources in the region of treatment tissue.

Alternatively, or in addition, data for positioning the light sources may be used for a realtime feedback during positioning, e.g. based on a image acquired during positioning, such as ultrasound based. Thus, an adaptation may be performed to the current patient situation when positioning the light sources. This is advantageous, for instance when the anatomical position should be changed since the initial acquisition of 3D data prior to the virtual planning of the number of light sources and position thereof.

The system may thus in another embodiment be a system for providing interstitial photodynamic and/or photothermal therapy on a region of tissue in a body. The system comprising at least one light source adapted to deliver a therapeutic light to said region of tissue in said tissue, wherein said light source is devised to be interstitially inserted into said tissue for interaction with a photosensitizer agent and/or for providing a controlled thermal environment of said tissue; and a unit for determining an optimized number of said light sources and individual position of each of said light sources in said region of tissue as well as individual control parameters for each of said light sources based on 3D or 4D image data of said region of tissue acquired by at least one image modality.

The 3D or 4D image data comprises said region of tissue and may be combined image data from at least two different image modalities.

As mentioned, the system may be adapted to provide said determination in a computer based virtual environment.

The system may comprise a unit for evaluating at least one photodynamic treatment parameter of said interstitial photodynamic therapy at said light source; a unit for modifying characteristics of said therapeutic light of said interstitial photodynamic therapy in response to the evaluation of said photodynamic treatment parameter; and a control unit that is arranged to restrict said delivery of therapeutic light treatment at least temporary in dependence of at least one attribute of one of said photodynamic treatment parameters.

The light source may be a distal end region of an optical fiber. The distal end region may comprise a light diffuser.

The light source may also be an implantable light source, such as a light diode, laser diode.

In an aspect, a computer based method of virtually planning a PDT session, comprises providing 3D or 4D data of a region of interest from at least one imaging modality, and determining a number and distribution of interstitial light sources for optimized treatment.

The method may comprise providing a template for position of the light sources in said region of interest.

The providing of a template may comprise producing said template based on production data that is output from said virtual planning.

Based on the virtual planning, the light sources are accordingly positioned in the region of treatment tissue.

This positioning may be provided by using a surgical template produced from production data that is output from said virtual planning. The production data may e.g. be provided in STL format. Production may be accomplished by free from methods, including rapid prototyping methods.

According to another embodiment of the invention, a computer program for processing by a computer is provided. The computer program comprises code segments for aggregating and accurately superimposing multidimensional images from different images modalities in a photodynamic pre-treatment of a subject, in a system for providing interstitial photodynamic therapy on tissue in a body. The computer program comprises a first code segment for evaluating at least two sets of multi-dimensional images of arbitrary image modality of the tumor site of a subject; a second code segment for aggregating said multi-dimensional images rendering a superimposed multi-dimensional; and a third code segment for determine positions of interstitial distal end of the optical fibers in said tumor of the subject.

In an example, a method is used where the decay of the transmitted light at increasing distances in the tissue is recorded and fitted to a model for light propagation. An embodiment of determining the number and position of light sources is based on such a model. A model that may be used is the transport equation for radiative transfer, as described in A. J. Welch and M. J. C. van Gemert: Optical-Thermal Response of Laser-Irradiated Tissue (Plenum Press 1995); and more specifically, an approximation based on the assumption of diffuse light propagation—the diffusion equation. The resulting data is the effective attenuation coefficient of the tissue, $\mu_{eff}$ evaluated using the equation $$-\ln(\phi_i r_i) = -\ln\left(\frac{P\mu_{eff}^2}{4\pi\mu_a r_i}\right),$$

wherein the index i denotes a measurement from a detector fiber i, and $r_i$ is the distance from the light source to each detector fiber, wherein i is an integer larger or equal to one, denoting the number of fibers used in the PDT system, such as six, twelve, eighteen, or more fibers. Moreover, P denotes the light output power of the therapeutic light source used for fiber I and $\mu_a$ is the absorption coefficient. By using $\mu_{eff}$ and the diffusion equation, the fluence rate may thus be calculated in the tissue.

The different setting, the initial settings and those during the treatment procedure, are stored for later calculation and further adjustment of the data base comprising the patient population data. In this effort complementing resources may be used, such as imaging modalities, e.g. MR, CT, Ultrasound, as well as long-term results. The data base comprising the patient population data is thus continuously updated and further improved to provide an optimal prediction.

In addition to the recorded fluorescence measurements, the three-dimensional geometry of the tissues for treatment are considered in the calculations, as well as the positions of the light sources and detectors, and the optical properties of the tissue itself. This data may for instance at least partly be provided from an imaging modality, such as Ultrasound, MR or CT.

Interstitial PDT (IPDT) is regarded an alternative to radical prostatectomy, external radiation and chemotherapy for the treatment of localized prostate cancer. For example, the photosensitizer agent Temoporfin (mTHPC, meso-tetra(hydroxyphenyl)chlorin) is used for treating secondary and primary prostate cancer. Utilizing bare-ended fibers, the delivered light doses were 20 to 100 J per treatment site, resulting in significant treatment induced necrosis and decreasing prostate-specific antigen (PSA) levels. By using diffusors, treatment time and number of fibers may be reduced. Four of six primary cases experienced only very minor complications, including transitory irritative voiding symptoms, whereas the more serious complications included stress incontinence and one case of deteriorated sexual function. For the secondary cases, PSA eventually started to increase again and tumor recurrences in 13 out of 14 patients required antiandrogen therapy post PDT. According to the authors, a more detailed drug and light dosimetry might lead to better discrimination between target tissue and surrounding sensitive organs.

Hence, there is a need for more accurate and individualized realtime dosimetry, both for PDT on prostate tissue and in more general terms. There are numerous reports on prostate in vivo spectroscopic measurements of parameters related to the PDT effect, e.g. light fluence rate, sensitizer distribution, and tissue oxygenation as well as blood flow and volume. Such studies hold great potential in increasing the understanding of the processes associated with PDT on prostate tissue and in extending clinical prostate-PDT to also incorporate individualized treatment dosimetry and realtime treatment feedback.

A finite element method (FEM) is utilized to simulate light transmission signals within a realistic prostate model for temporally and spatially varying tissue optical properties. Based on the simulated data set, the ability of the algorithm is verified to be capable of tracking an increase in the effective attenuation coefficient within the prostate gland. Furthermore, via tissue importance weighting within the Block-Cimmino algorithm the possibilities to discriminate between target tissue and organs at risk (OAR) in terms of the deposited light dose is evaluated. Finally, the dose volume histograms (DVHs) of the light dose delivered during an IPDT treatment with a simulated absorption increase are compared with and without treatment feedback. In this way, the feasibility is determined for an IPDT dosimetry model that ascertains a certain predetermined light dose within the target tissue irrespective of any treatment-induced changes in tissue absorption.

Figure 2:
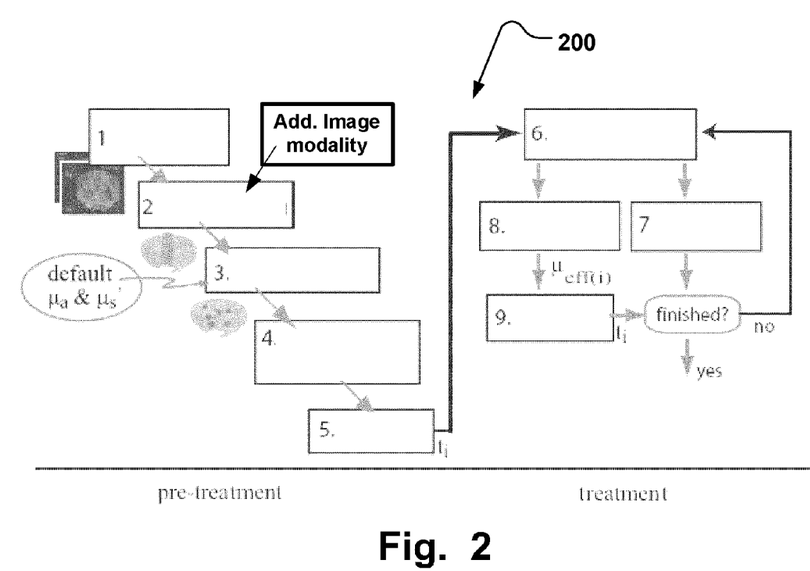
FIG. 2 is a flow chart illustrating the pre-treatment planning as well as the treatment and monitoring sequences that constitute the realtime dosimetry module.

The IPDT treatment 200 as outlined in FIG. 2 comprises dosimetry software has been developed to execute on the aforementioned IPDT apparatus that utilizes a maximum of 18 optical patient fibers. The patient fibers may for instance be bare-ended 400-μm diameter optical fibers for delivery of therapeutic light. Alternatively, or in addition, diffusors may be used. The therapeutic light may be around 652 nm, matching one of the absorption bands of the photosensitizer Temoporfin. By means of internal optical units, the instrument may switch between treatment mode, during which all fibers emit therapeutic irradiation, to diagnostic measurement mode, wherein one fiber at the time is active and six neighboring fibers detect the transmitted light. The detection unit consists of six spectrometers covering the spectral interval between 630 and 840 nm.

The treatment session consists of pre-treatment and treatment procedures where a graphical user interface guides the urologist through the treatment procedure.

At first, a first 3D data set comprising the region of treatment is acquired from a first imaging modality. For instance, an ultrasound investigation of a prostate is performed to assess the geometry of the target tissue as well as nearby OAR, step (1). Within a set of 6 to 10 ultrasound images, the urologist may delineate the extent of the prostatic gland, urethra, rectum, upper and lower sphincters and the cavernous nerve bundles in a computer based virtual treatment planning.

Additionally, a second 3D data from a different image modality comprising the region of treatment may be used to further improve the virtual planning. Matching of the two 3D data sets may be made by known image processing algorithms, e.g. based on grey scale based matching, surface matching, object matching, etc. The combined 3D data set may facilitate improved virtual planning as e.g. different anatomical structures are combinable in a single 3D image. For instance, bone tissue and soft tissue may be provided in a single 3D image (e.g. from CT and MR image modalities).

The tissue contours are then patched into a three-dimensional voxel representation of the geometry containing all organs, step (2).

A search algorithm calculates the near-optimal source fiber positions within the reconstructed geometry, step (3). The virtual planning of the light sources positioning in the 3D model may be made automatically, or semi-automatically. The resulting positions may then be transferred from the virtual planning to the real surgical situation as the patient is prepared for the treatment. By providing a surgical template as described herein, the precision of positioning may be improved.

Figure 3:
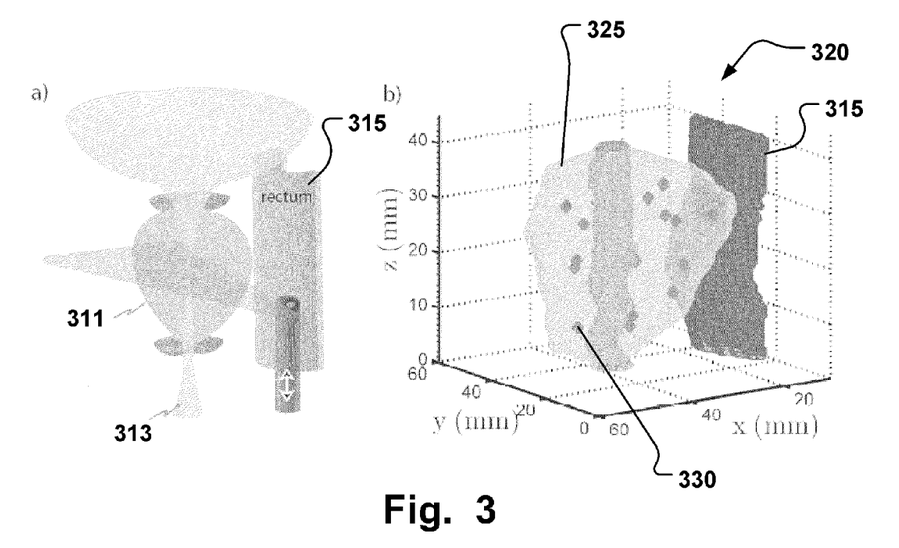
FIG. 3a is a schematic drawing of organs incorporated into a prostate dosimetry model.
FIG. 3b is a three dimensional graph that shows the reconstructed geometry of a patient target site.

FIG. 3 illustrates a sample three-dimensional geometry model 320, with 1 mm voxel side lengths, including the target tissue 325, i.e. the prostate 311, the OAR, consisting of the urethra 313, rectum 315, and normal, surrounding tissue as well as the source fiber positions 330. This geometry, representing the "test" geometry used in this work, was created based on eight ultrasound images from a patient with a glandular volume of approximately 27 cm³ and treatment fiber positions were calculated by the algorithm described in Section C.

Utilizing hollow steel needles, the optical fibers, also referred to as treatment fibers, are guided into position, step (4). This may be done by using a surgical template. Within this fourth step, the urologist is given the opportunity to update the final fiber positions as these might deviate slightly from the set of positions calculated by the random-search optimization algorithm. Information on the geometry and the actual fiber positions is used as input for the Block-Cimmino optimization algorithm to predict required irradiation times for all source fibers, step (5).

B. Geometry Model

The geometry model is a three-dimensional voxel representation of the target organ, here the prostate, and the adjacent urethra, rectum, upper and lower sphincters and the cavernous nerve bundles, as risk organs. Several image modalities may be used in rendering an anatomical accurate 3D model of the target organ. By e.g. superimpose an ultrasound image with a MRI or a PET image or a SPECT image or any other suitable image modality. In the description below an ultrasound image is the basis for explaining the invention. When manually or semi-automatically determining the organ positions in the 3D patient data set, the physician for instance marks five to twenty points, within six to ten ultrasound images, delineating the periphery of the different tissue types present in that particular cross-section. These points are then connected by linear interpolation to form connected organ contours. From the ultrasound investigation, the transversal images are craniocaudally separated by five mm.

Precision may be improved by having combined 3D data from several image modalities.

The tissue contours may be linearly interpolated to regions in between ultrasound cross-sections, giving voxel side lengths of 1 mm in all three dimensions. A filling technique is applied to specify the tissue type for voxels within the delineated contours; first every voxel within the three-dimensional matrix is initiated to normal tissue except for voxels containing the contours of any other tissue type. Then, the center of each set of contour points is calculated. For each tissue type, the following procedure is executed; first, the center point of the current tissue type is put in a buffer. The first point in the buffer is then extracted and set to the same tissue type as the current tissue type. Thereafter its six connected neighbors are tested for tissue type. If a point does not belong to the same tissue type as the current contour point and does not belong to another set of contour points it is put into the buffer. This procedure is repeated until the buffer is empty, thus filling every tissue type from its center and outwards. The reconstructed voxel model has typical side lengths of 60-65 voxels.

TABLE 1

Tissue specific weights ($\omega_j$)used for optimizing fiber positions, fluence range (lower value $L_j$ and upper value $U_j$, and weights ($\alpha_j$)used for the Cimmino optimization algorithm.

| Tissue type | $\omega_j$ | $L_j$, $U_j$(J/cm²) | |
|---|---|---|---|
| Normal tissue | 0 | 0-5 | 1e−4 |
| Upper sphincter | −1 | 0-5 | 0.1 |
| Lower sphincter | −1 | 0-5 | 0.2 |
| Rectum | −1.7 | 0-5 | 0.1 |
| Prostate | 1 | 5-Inf | 2 |
| Urethra | −0.85 | 0-5 | 0.1 |

C. Fiber Positions

The task of finding the optimal fiber positions may be formulated as maximizing the light fluence rate within the target organ, here the prostatic gland, while minimizing the light distribution within the organs at risk (OAR) adjacent the target organ to be treated. The optimization algorithm is an iterative random-search algorithm similar to a simulated annealing type algorithm. The search for optimal fiber positions is initialized by creating a random configuration of source positions within the prostate. In the description below an embodiment is described with reference to the distal ends of the fibers being point sources. Configuring the distal ends to emit diffused light slightly alters the basic physics for the algorithm, although the basic concept rendering fiber tip positions are unchanged. However, using diffusors may minimize the treatment energy, treatment time, as well number of light sources, such as fibers needed.

The bare-ended fibers are modeled as isotropic point sources where the fluence rate in voxel j due to a source in voxel i, $\phi_{ij}$, is approximated by the analytical solution to the diffusion equation within an infinite, homogeneous medium:

$$\phi_{ij} = \frac{P\mu_{eff}^2}{4\pi\mu_a r_{ij}}\exp(-\mu_{eff}r_{ij}), \tag{1}$$

wherein P denotes the light source effect, set to 0.15 W in this example, and the effective attenuation coefficient is given by $\mu_{eff}=[3\mu_a(\mu_a+\mu'_s)]^{1/2}$, where $\mu_a$ and $\mu_a'$ were set to 0.5 and 9.7 cm⁻¹, respectively. For every iteration, each fiber is moved a limited length in a random direction.

The movement is restricted to voxels within the prostate and only one source fiber per voxel is allowed. Following a fiber movement, a fitness value is computed to evaluate the quality of the configuration:

$$F = \sum_{j=1}^{M}\omega_j^{target}\phi_{ij} + \sum_{j=1}^{N}\omega_j^{OAR}\phi_{ij} \tag{2}$$

The first summation in equation (2) includes 25% of the prostate voxels with the lowest fluence rate. The target target tissue weights, $w_{ij}^{target}$, are positive, contributing constructively to the fitness value when delivering light to this particular region. Correspondingly, the second summation in formula (2) includes 25% of the voxels within OAR, i.e. the urethra, rectum, upper and lower sphincters and the cavernous nerve bundles, characterized by the highest fluence rate. The corresponding tissue weights are given in Table 1 above, where each $w_{ij}^{OAR}<0$, thereby causing any fluence rate within organs at risk to punish the overall fitness function value. Equation (2) thus seeks to maximize the lowest fluence rate values in the prostate while minimizing the highest fluence rate values outside the target tissue.

For the iterative scheme, the new fiber positions are accepted only if a fiber movement leads to a higher fitness function value. As the light distribution may be considered diffuse at the earliest a distance $1/\mu'_s$ from the fiber tip, the resulting fiber positions are presented with the depth coordinate decreased by this distance.

Random-search algorithms of this type are not guaranteed to find the global optimum. However, the stochastic movements increase the probability that the search may find its way out of a local optimum. In the current implementation the maximum step size is decreased gradually from three to one voxel to ensure that the solution will converge to an optimum, although this is at the expense of the ability to circumvent local optima. Typical execution times were on the order of 45 to 60 minutes, but may be minimized by alternative or future calculation hardware improvements.

Figure 4:
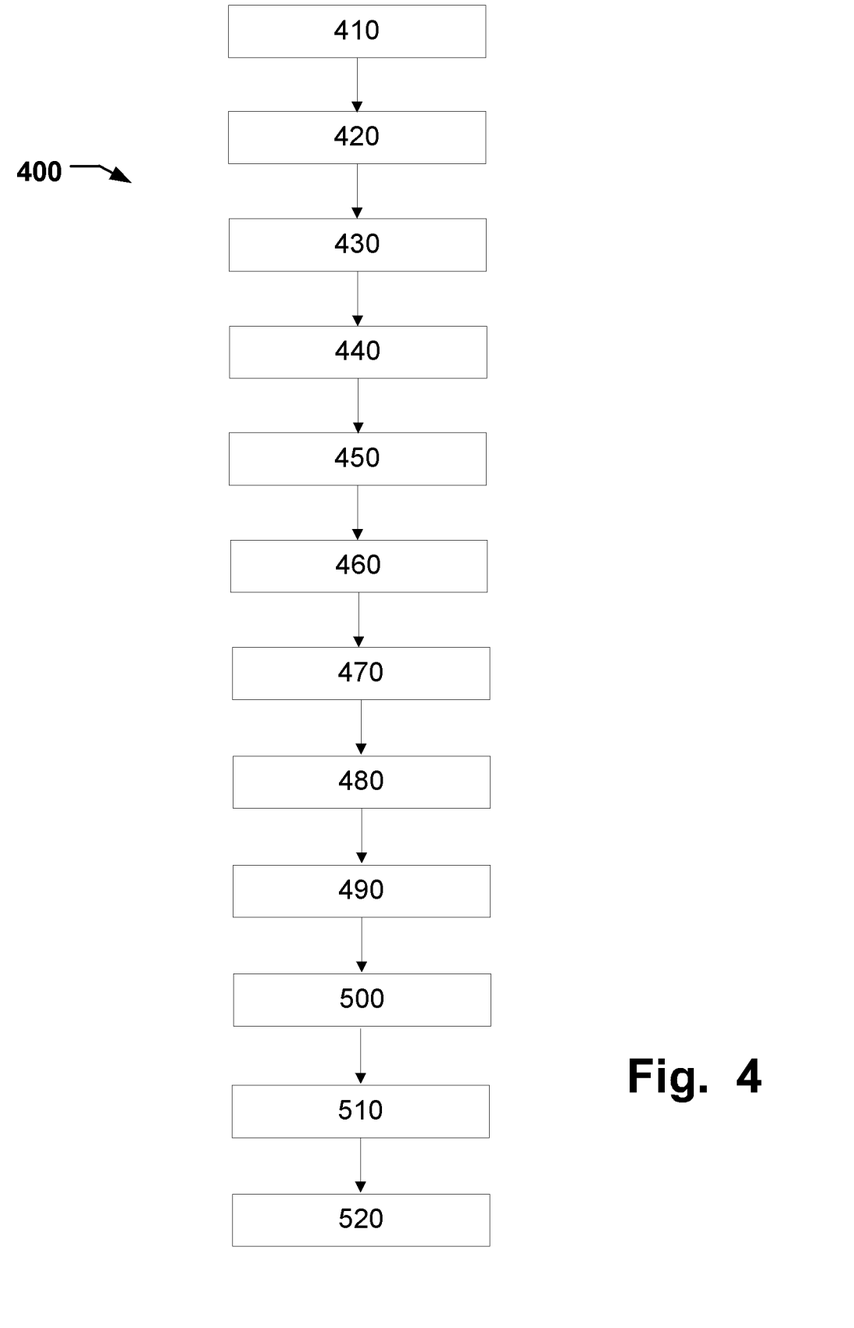
FIG. 4 is a flow chart of an embodiment of a method 400 comprising steps 410-490 and 500-520.

FIG. 4 further illustrates the method discussed above in sequential steps 400, although it should be apparent for a skilled person in the art when reading the present disclosure that same steps could be performed overlapping each other. The method begins with acquisition of 3D or 4D image data from the first image modality 410. From the acquired image data the anatomic structures are delineated 420 by a physician. The resulting data is stored in the system. This step can also be semi or fully automatic depending on e.g. complexity of the images and/or available computer capacity. The following step 430 is for acquisition of 3D or 4D image data from the second image modality, different image modality than the first. This step is followed by delineation in the data image 440, performed as in 420 above. The following step 450 and 460 represents acquisition of image data and further delineation if additional image modalities different from the above are to be used.

Matching of the 3D or 4D data sets is then executed 470 and may be made by known image processing algorithms, e.g. based on grey scale based matching, surface matching, object matching, etc. The combined 3D or 4D data set may facilitate improved virtual planning as e.g. different anatomical structures are combinable in a single 3D or 4D image. The tissue contours are then patched into a three-dimensional voxel representation of the geometry containing all organs, step 480. At this stage the pre-treatment method determine distribution and number of interstitial light sources 490 to be applied within the tissue taken into account the OAR. Having the position and number of interstitial light sources a template may be processed 500. However, alternatively, or in addition, data for positioning the light sources may be provided for a robotic system automatically or semi-automatically positioning the light sources in the region of treatment tissue.

The pre-treatment is now completed and the treatment session may commence 510, based on the initial values determined in previous steps. During the treatment session intermediate feedbacks to ascertain a certain predetermined light dose is within the target tissue irrespective of any treatment-induced changes in tissue absorption is performed 520. It should be apparent for a person skilled in the art when reading the present disclosure that step 520 may slightly change the initial values depending on treatment-induced changes in the tissue. The new values are provided into the treatment settings to optimize the present treatment.

A new treatment session may be started after a healing period or diagnosis to evaluate the effect of therapy achieved during the treatment session.

In conclusion, a method and system is presented that constitute an initial pre-treatment procedure and/or planning process dosimetry module for IPDT, in an embodiment on the whole prostate glandular tissue. Implemented on an 18 fiber IPDT apparatus, the dosimetry software includes positioning individual distal tips of optical fibers. Delivery of light dose may take into account patient-specific anatomy by superimposed images from several images modalities to initially accurately pre-set the PDT treatment parameters. Utilizing data on light distribution simulated by the FEM within a realistic prostate model have shown that increasing levels of light attenuation may be tracked. A different number of optical fibers may be used in other embodiments.

As will be appreciated by one of skill in the art, the present invention may be embodied as a device, system, method or computer program product, eventually as a medical workstation or at least partly comprised therein. Accordingly, the present invention may take the form of an entirely hardware embodiment, a software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Embodiments of the present invention are described herein with reference to flowchart and/or block diagrams. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the diagrams may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A system for providing interstitial photodynamic and/or photothermal therapy on a region of tissue in a body, said system comprising:
   at least one light source adapted to deliver a therapeutic light to said region of tissue in said tissue, wherein said light source is devised to be interstitially inserted into said tissue for interaction with a photosensitizer agent and/or for providing a controlled thermal environment of said tissue; and
   a unit for determining an optimized number of said light sources and individual position of each of said light sources in said region of tissue as well as individual control parameters for each of said light sources based on 3D or 4D image data of said region of tissue acquired by at least one image modality, wherein said 3D or 4D image data comprises said region of tissue and is combined image data from at least one image modality.

2. The system of claim 1, wherein said system is adapted to superimpose said 3D or 4D image data for obtaining said combined image data from at least two different image modalities.

3. The system according to claim 1, wherein said system is adapted to provide said determination in a computer based virtual environment.

4. The system according to claim 1, further comprising
   a unit for evaluating at least one photodynamic treatment parameter of said interstitial photodynamic therapy at said light source;
   a unit for modifying characteristics of said therapeutic light of said interstitial photodynamic therapy in response to the evaluation of said photodynamic treatment parameter; and
   a control unit that is arranged to restrict said delivery of therapeutic light treatment at least temporary in dependence of at least one attribute of one of said photodynamic treatment parameters.

5. The system according to claim 1, wherein said light source is a distal end region of an optical fiber adapted to be inserted interstitially into said region of tissue.

6. The system according to claim 5, wherein said distal end region comprises a light diffuser such that said optical fiber is configured at the distal end to emit diffused light.

7. The system according to claim 1, wherein said light source is an implantable light source.

8. A non-transitory computer readable storage medium having stored thereon a computer program configured for planning an interstitial photodynamic and/or a photothermal therapy session on a region of tissue in a body, said computer program comprising
   a first code segment for evaluating at least one set of images of one image modality of the tumor site of a subject;
   a second code segment for aggregating said images rendering a superimposed multi-dimensional 3D or 4D image data set; and
   a third code segment for determining an optimized number of said light sources and individual position of each of said light sources in said region of tissue as well as individual control parameters for each of said light sources based on said superimposed image data set.

9. A computer based method of virtually planning an interstitial photodynamic and/or a photothermal therapy session on a region of tissue in a body in a virtual environment, said method comprising
   providing 3D or 4D data of a region of interest from at least one imaging modality;
   determining a number and spatial distribution, position and spatial orientation of interstitial light sources in relation to said region of tissue for optimized treatment based on an optimized number of said light sources and individual position of each of said light sources in said region of tissue as well as individual control parameters for each of said light sources based on a superimposed image data set; and
   virtually planning said session on said determined number and spatial distribution, position and spatial orientation of said interstitial light sources.

10. The method according to claim 9, comprising providing a virtual template for virtually simulating positioning of the light sources in said region of interest based on said virtual template.

11. The method according to claim 10, wherein said providing a virtual template comprises providing production data for said template based on said virtual planning.

12. The method according to claim 10, wherein said virtual planning comprises virtually simulating positioning said template in relation to said region of tissue, and virtually simulating introduction of said light sources into said region of tissue.

13. The method according to any of claims 10, wherein said 3D or 4D data comprises image data for a region comprising a region of treatment where said region of tissue is located, and wherein said virtual planning comprises virtual planning of affixing said template on anatomically fixed positions.

14. The method according to claim 10, wherein said virtually planned template comprises at least one guide unit having a defined stop unit.

15. The method according to claim 9, comprising virtually positioning the light sources and providing data for a robotic system for automatically or semi-automatically positioning the light sources in the region of treatment tissue in a real medical procedure.

16. A method of producing a template based on production data from said method of virtual planning according to claim 9.

17. The method of claim 16, wherein said production of said template is made by free from methods, including rapid prototyping methods.

18. A medical procedure comprising the virtual planning of claim 9, further comprising positioning the light sources accordingly in the region of treatment tissue based on data from said virtual planning.

19. The method of claim 18, further comprising positioning a template produced from production data that is output from said virtual planning in relation to said region of treatment tissue.

20. A system for virtually planning interstitial photodynamic and/or photothermal therapy on a region of tissue in a body, said system comprising:
   a unit for processing 3D or 4D data of a region of interest from at least one imaging modality;
   a unit for determining a number and spatial distribution, position and spatial orientation of interstitial light sources in relation to said region of tissue for optimized treatment based on an optimized number of said light sources and individual position of each of said light sources in said region of tissue as well as individual control parameters for each of said light sources based on a superimposed image data set; and a unit for virtually planning said session on said determined number and spatial distribution, position and spatial orientation of said interstitial light sources.

* * * * *

UNITED STATES PATENT AND TRADEMARK OFFICE
CERTIFICATE OF CORRECTION

| | |
|---|---|
| PATENT NO. | : 8,582,841 B2 |
| APPLICATION NO. | : 12/836497 |
| DATED | : November 12, 2013 |
| INVENTOR(S) | : Johannes Swartling |

It is certified that error appears in the above-identified patent and that said Letters Patent is hereby corrected as shown below:

In the Specification

At column 1, line 9, please delete "Feb. 13, 2009," and insert therefore, --Oct. 29, 2010--.

At column 6, line 34, please delete "treatment" and insert therefore, --treatment.--.

At column 12 (TABLE 1), line 2, please delete "($\omega_j$)used" and insert therefore, --($\omega_j$) used--.

At column 12, line 45, please delete "$\mu_a'$" and insert therefore, --$\mu_s'$--.

At column 12, line 59, please delete "target target" and insert therefore, --target--.

In the Claims

At column 16, line 32, please delete "any of claims" and insert therefore, --claim--.

Signed and Sealed this
Seventeenth Day of June, 2014

Michelle K. Lee
*Deputy Director of the United States Patent and Trademark Office*